United States Patent [19]

Cushman

[11] 4,239,971

[45] Dec. 16, 1980

[54] SIMULTANEOUSLY DISPLAYING VARYING TOMOGRAPHIC IMAGES OF DENTAL ARCH WITH SINGLE PANORAMIC X-RAY EXPOSURE

[75] Inventor: Robert H. Cushman, Princeton, N.J.

[73] Assignee: Pennwalt Corporation, Philadelphia, Pa.

[21] Appl. No.: 82,373

[22] Filed: Oct. 5, 1979

[51] Int. Cl.³ .............................................. G03B 41/16
[52] U.S. Cl. ........................ 250/439 P; 250/416 TV; 250/445 T
[58] Field of Search ........ 250/439 P, 416 TV, 445 T; 358/111

[56] References Cited

U.S. PATENT DOCUMENTS 4,196,351  4/1980  Albert ............................... 250/439 P

*Primary Examiner*—Craig E. Church

[57] ABSTRACT

Only a single panoramic exposure to an X-ray source is needed to simultaneously provide a plurality of different real time and/or permanently recorded tomographic images of a focal trough of a patient's dental arch area. Contrast, intensity and magnification properties relating to tissue, bone, teeth, cheeks, and the like, may readily be varied by the dentist, physician or medical technician by merely turning or adjusting appropriate knobs of electronic components associated with the invention, a task impossible to achieve by present direct film screen X-ray cameras.

16 Claims, 7 Drawing Figures

$D_1 = D_2 = D_3 = \sim .0005"$ TO $.015"$

SIMULTANEOUSLY DISPLAYING VARYING TOMOGRAPHIC IMAGES OF DENTAL ARCH WITH SINGLE PANORAMIC X-RAY EXPOSURE

STATEMENT OF INVENTION

This invention relates to radiography and more particularly to apparatus and methods for simultaneously providing multiple differing tomographic panoramic images of the dental arch with only a single X-ray exposure.

BACKGROUND AND SUMMARY OF THE INVENTION

In conventional panoramic dental radiography, an X-ray source and camera extend from opposite sides of an arm which rotates slowly above the patient's head such that X-radiation from the X-ray source passing through the dental arch area is continuously received by the camera. The X-ray film within the camera is driven at a predetermined non-linear speed past a centrally disposed slot in a front panel of the camera. The patient may or may not be shifted during the orbiting of the X-ray source and camera about him. When the equipment is correctly adjusted and the patient properly disposed, one curved layer or curved plane of the dental arch area will be in focus while layers on either side thereof become progressively blurred as the distance from the layer in focus increases, i.e., a tomographic image of the desired layer is obtained.

That curved layer or plane in focus is commonly referred to as the focal trough, i.e., the selected sharp layer lying in a vertical curved plane having a horizontal dimension or width designed to portray radiographically, part of the bone of the maxilla, part of the bone of the mandible, and the teeth.

A clear image or view of the focal trough provides the dentist with extremely valuable diagnostic information. However, currently available apparatus do not provide sufficiently sharp images having adequately wide troughs, especially in the anterior region, nor do current techniques provide for rapid real time changes in focal trough locations or shapes as the image is formed on the oscilloscope display. In film systems, the image is not normally seen until after the patient exposure is completed since the image is recorded on X-ray film.

The present invention substantially overcomes the aforementioned disadvantages and weaknesses of the prior art by providing apparatus and methods which permit the dentist to observe real time displays of a plurality of different focal trough images simultaneously as the images are created, and wherein the created images may be controllably varied to provide optimum diagnostic information by simply adjusting knobs of associated electronic components. Additionally, hard copies of desired images can readily be made available.

BRIEF DESCRIPTION OF THE DRAWINGS

FIGS. 4, 5 and 6 illustrate how the wobbulated sweeps of FIG. 3, when continuously applied to the cathode ray beam forming the moving slot image, focus a single plane of the object being radiographed and progressively blur other layers more distant therefrom.

DETAILED DESCRIPTION OF THE INVENTION

Figure 1:
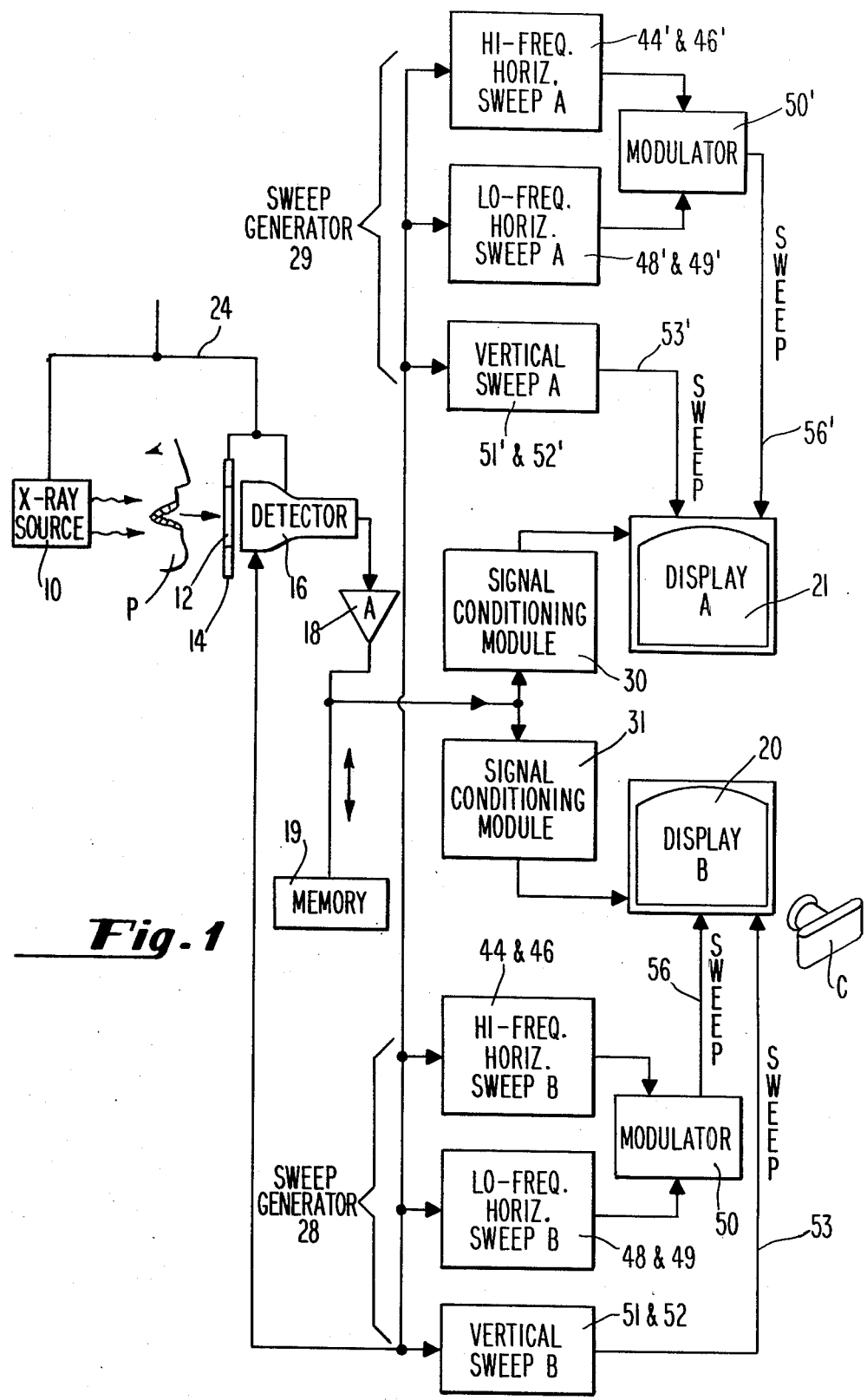
FIG. 1 is a diagrammatic representation of an embodiment of the panoramic X-ray unit of the invention.

In FIG. 1, an X-ray source 10 contained within a tubehead generates X-radiations which penetrate the dental arch area of a patient P and enter slot 12 which suppresses stray radiation. Slot 12, if a conventional camera 14 is used with X-ray film therein, will be centrally vertically disposed in a front panel member of the camera assembly. Such camera assembly will provide conventional panoramic radiographs. The X-ray film will be driven within the camera at a predetermined non-linear speed, the film drive mechanism for driving the film forming no part of the present invention. Normally however, X-ray film with conventional intensifying screens will not be employed with the present invention.

In the present invention, the X-radiation or beams passing through slot 12 enter detector 16. The input screen of X-ray detector 16 is scanned electronically to provide an electrical output signal proportional to the intensity of the incoming X-ray energy. The input screen is scanned by means of conventional horizontal and vertical sweep drive circuits which are synchronized with the sweep circuits of the cathode ray oscilloscope output displays, later described. The output signals from detector 16 are then amplified by conventional amplifiers 18 for modulating or controlling the intensity of the oscilloscope displays, one or more of which displays may be used. Other types of electronic image display systems may also be utilized with the present invention, such as a liquid crystal display, and the like.

The present invention needs no conventional panoramic camera assembly, film, and film drive mechanism. It is understood that input screen of detector 16 is disposed in close operable proximity to slot 12, preferably flush-mounted thereagainst and aligned therewith in order to receive the radiation energy passing therethrough. X-ray source 10 is mounted on one end of arm 24 while collimating slot 12, detector 16, and amplifiers 18 are mounted or carried at its other end for rotation as a unit therewith such that generated radiation from source 10 will penetrate the dentral arch of patient P for reception by detector 16 after passing through slot 12. A memory 19, later described, may be disposed after amplifiers 18.

Radiation energy passing through slot 12 is constantly changing as X-ray source 10 slowly orbits the patient's head, i.e., the denser the object being irradiated such as bone and teeth, as compared with cheeks or lips, the greater will be the quantum of X-radiation absorbed by the denser object, with a corresponding lesser amount of X-radiation received by detector 16, thus resulting in a less dense image of the object at that point. If the instantaneous radiation energy at slot 12 were to be converted to an image, it would appear as a bar pattern on the oscilloscope display having substantially the same dimensions as slot 12, i.e., approximately ¼"×5" with the intensity at each point of the image corresponding to the density of the patient along the axis of X-rays at that point. This bar pattern, hereinafter referred to as the "slot image", will electronically be caused to move across the entire length of the display screen 20, and/or 21, etc., in a period no greater than about 20 seconds, which represents the maximum time consumed by the 240° rotation of the tubehead, which contains the X-ray source 10, in scanning the entire dental arch; or in a period as short as about 4 seconds. It is understood that the 240° rotation of the tubehead is an approximation, and a greater or lesser angular rotation may be considered. Typically, displays 20 and 21, B and A respectively in FIG. 1, measure approximately 5"×10", to thus portray life-sized images of the dental arch.

The varying speed at which the slot image moves across the display screens is controlled in order that the desired layer or plane in the object being radiographed is in sharp focus, while layers on either side thereof will be progressively blurred as the distance therefrom increases.

It should be appreciated that the varying speeds at which the slot image is swept across the oscilloscope display screens corresponds to the non-linear speed at which the X-ray film in a conventional panoramic dental X-ray camera is caused to move past the slot in the camera.

To further clarify, in conventional panoramic dental X-ray machines, the non-linear speed at which the film is driven past the camera slot controls the location and shape of the layer or plane in focus of the object being radiographed. By varying this non-linear speed, the location and shape of the layer or plane in focus is varied, other factors remaining constant, including position of patient P. It should be recognized that the magnification of the image varies with the distance of the focal trough to the detector and to the source as in conventional film systems. Similarly, by varying the non-linear speed at which the slot image is swept across the screens of the oscilloscope displays, the location and shape of the layer or plane of the object being radiographed which is in sharp focus is varied or controlled. Hence, the electronic horizontal sweep circuits for displays B and A may be considered electrical analogs to the film drive systems in conventional panoramic dental X-ray machines. It is recognized by those skilled in the art that it is most difficult to vary location and shape of the focal trough, i.e., the layer or plane of the dental arch in focus in present day mechanical panoramic dental X-ray systems, since cams, gears, levers and the like, must be changed or adjusted. In the present electronic system, it should be appreciated that by adjustment of a simple electronic control, wide changes in both location or shape of the focal trough or layer or plane of the object in focus can be readily and rapidly accomplished either in real time as the image develops on the display, or after the fact.

The use of a single oscilloscope display is suitable for the simplest applications since it reveals all the information provided by present day mechanical panoramic dental X-ray machines. The use of two or more displays, as illustrated in FIG. 1, for example, allows the simultaneous presentation of two or more different locations or shaped focal troughs or layers or planes in focus. By selecting differing horizontal sweep instantaneous non-linear speeds or wave shapes for each display, simultaneous views of different focal troughs with but a single exposure of the patient may be provided.

The present invention lends itself admirably to electronic memory storage systems. Memory 19 may be an electronic memory, with or without hard film permanent record associated therewith; or motion picture film record, tape storage, holographic storage, or any other conventionally available high resolution permanent storage media. The stored output signals from detector 16 and amplifier 18 may be "played back" after the radiation scan of the patient has been completed and displayed on display screens 20 and 21. Thus, it is now possible to inspect the display of a focal trough of a given patient, and, if desired, by manipulation of appropriate electronic controls, change the location of a portion or of the entire focal trough until the areas of optimum interest are brought into sharp focus. Such panoramic tomographic displays are not believed available with any other prior art dental X-ray machine.

Each instantaneous detector scan of the radiation which strikes input screen of detector 16 may be considered a single image. One may then consider the complete display to consist of a combination of a large number of these images overlapping in a synchronized fashion. Hence, all the information from each individual slot image stored in the memory can be combined to provide an almost unlimited series of views of different focal trough locations and shapes of a given patient after only a single X-ray scan of that patient and after the patient is no longer present. The number of views available and the resolution chosen for each view determine the number of bits of information needed for storage, and, along with the size of memory chosen, contribute in determining the total capacity of the overall system.

The cathode ray oscilloscope displays provide an additional advantage, i.e., the intensity and contrast of the resultant image can be varied to suit. It should be recognized that by intentionally utilizing a non-linear amplifier or filter, it becomes readily possible to emphasize or de-emphasize specific density levels, to vary contrast, to magnify or demagnify specific areas of interest, such, for example, as emphasizing tissue versus bone, bone versus tissue, and the like. Further, subtractive, zoom magnification, or other comparative processes can be utilized to delineate or emphasize specific areas of interest or to identify only those areas which have changed. A variety of other electronic image enhancement techniques can also be readily applied. Signal conditioning modules 30 and 31, for example, are shown in FIG. 1.

It should be borne in mind that the capability of the present invention to store patient data using only a single panoramic X-ray exposure and then to create a series of new and meaningful focused tomographic images therefrom through the use of wobbulated sweep voltages, later described, is considered a significant advance in the dental and medical arts. The much recently publicized CAT scanners, for example, still require multiple scans in order to produce multiple views. The basic principle of panoramic radiography or tomography employs synchronized movements of the X-ray source and detector. The present invention employs an X-ray source having a predetermined rotational speed which does not necessarily determine the image focal trough location or shape which can be changed at will when recalling the patient data from memory by control of the horizontal display sweep 56 wave shape. The usefulness of the present system is thus greatly enhanced since a significant number of different views of the same patient from a single X-ray scan is now available to the dentist or doctor, in addition to the advantages already made available from signal conditioning techniques abovementioned, including varying contrast, additive and subtractive techniques, non-linear gain techniques, noise elimination techniques, and others known in the art. Without a memory, two or more different focal trough views are now possible as well as a real time change of focal troughs as the image develops. It is emphasized again that the capability of providing different focal trough views from memory 19 is possible in a panoramic system only, and is not possible with periapical or bite wing systems of the prior art employing a stationary source.

Figure 2:
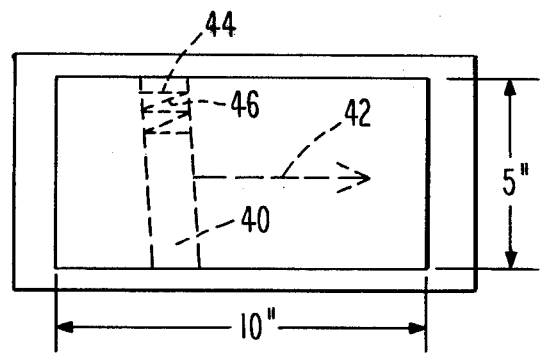
FIG. 2 is a diagrammatic representation of the cathode ray oscilloscope display screen of FIG. 1 portraying movement of a slot image thereacross.
Figure 3:
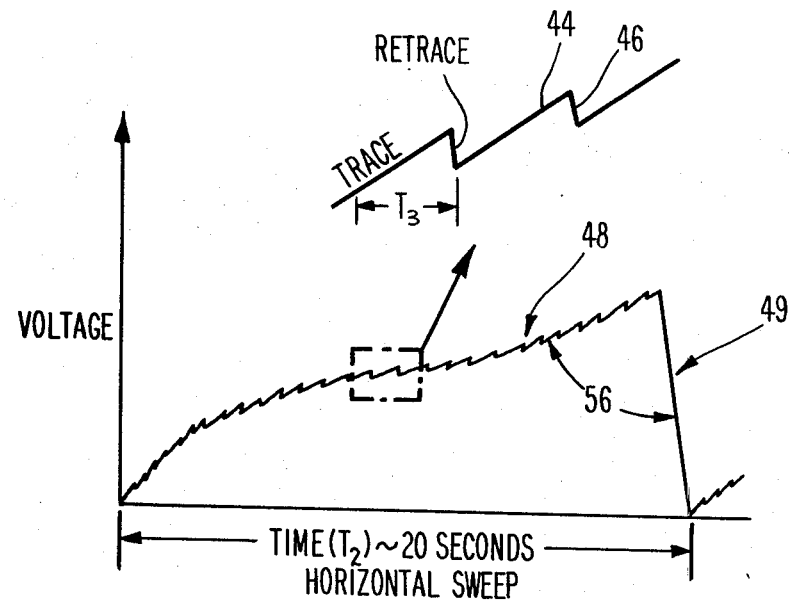
FIG. 3 graphically illustrates wobbulated sweeps which scan the oscilloscope display area shown in FIG. 1.
Figure 7:
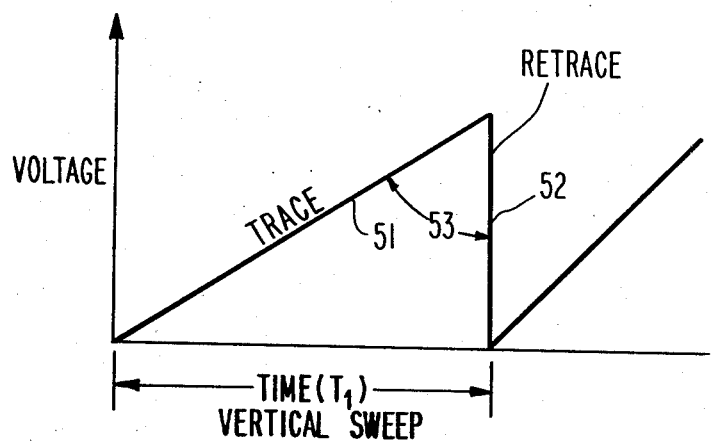
FIG. 7 graphically illustrates a wobbulated vertical sweep pattern for scanning a typical slot image of approximately $\frac{1}{4}'' \times 5''$ dimensions.

More specifically, and referring yet to FIG. 1, and additionally to FIGS. 2 and 3, slot image 40, measuring approximately $\frac{1}{4}"\times 5"$, is caused to move across oscilloscope display screen 20 in the direction of arrow 42. Sweep generator 28 is capable of generating two simultaneous sweep voltages, i.e., a high frequency horizontal sweep 44 and 46 (synchronized with the horizontal sweep in detector 16) which modulates or wobbulates a low frequency horizontal sweep 48 and 49, which effect movement of slot image 40 slowly across screen 20, in a manner somewhat akin to the controlled movement of X-ray film past a slot in a panoramic X-ray camera; and simultaneously therewith, two vertical sweep voltages 51 and 52 (FIG. 7) synchronized with the vertical sweep in detector 16. A modulator 50 combines the high and low frequency horizontal sweeps to provide sweep 56.

Thus, when horizontal and vertical sweeps 44, 46, 48, 49; and 51 and 52 respectively are applied to the cathode ray oscilloscope display 20 at a sufficiently high rate, an illusion is created on its screen of a continuous image. Typically, the time for horizontal sweeps 44 and 46 to scan once across the $\frac{1}{4}"$ slot image 50 consumes about 2.5 to 75 microseconds ($T_3$) and the totality of its vertical sweeps 51 and 52 for scanning the image 40 would require from 1 to 30 milliseconds ($T_1$-FIG. 7). The aforementioned time durations are exemplary, it being understood, of course, that actual sweep times will be chosen, as well as the wave shapes of the sweep voltages, to provide a desired focal trough shape and desired resolution. A typical minimum resolution is 3.0 line pairs/mm, or higher.

Sweeps 44, 46, 48 and 49 are introduced into the cathode ray oscilloscope to thus cause slot image 40 to travel across the entire 10" of display screen 20 in approximately 20 seconds ($T_2$). A wobbulated horizontal combined sweep 56, resembling a combined fine and coarse saw-tooth (FIG. 3) is provided, where the high frequency horizontal sweeps are indicated at 44 and 46 (trace and retrace respectively) and the low frequency horizontal sweeps are indicated at 48 and 49 (trace and retrace respectively). Sweep 48 could be linear; or non-linear as shown, and designed such that its changing waveshape may be adjusted in accordance with the desired location and shape of the focal trough. It is noted that the frequency of sweep 57 is usually constant such that the slot image is always at the end of its travel on the 10" display screen simultaneously with the 240° rotation of the X-ray source. However, the length of display may be varied for different magnifications, if so desired.

Sweep generator 29 (FIG. 1) is controlled to provide horizontal and vertical sweep voltages, similar to generator 28, for providing desired displays on display A simultaneously with displays on display B. It is noted that the sweeps from detector 16 are synchronized with the display sweeps, i.e., sweeps 44, 46, 51 and 52 for display B, and sweeps 44', 46', 51' and 52' for display A. Thus where detector 16 scans a spot X, for example, on a bar pattern of the slot image on its input screen, the spot X will be at the same relative location on the display screens' bar display.

Refer now to FIG. 4. An imaginary image frame 60 (not drawn to scale), having dimensions equivalent to slot 12, i.e., about $\frac{1}{4}"\times 5"$, is provided with two imaginary points, $A^1$ and $B^1$, arbitrarily selected. FIG. 5 additionally illustrates a succeeding image frame 62 occurring about one millisecond later and shows the same two points displaced slightly to the right on the screen due to the rotation of the tubehead about the patient. If the displacement of a point on screen 20 is equal in magnitude to the displacement of that point in frames 60 and 62, then the two images of the same point on the display screen will be superimposed and in focus.

If however, rotation of the tubehead around patient P causes a larger or lesser magnitude displacement of the points on display screen 20 as compared to their frame displacement on the screen, the images of that point will be displaced on the display screen and consequently will be blurred, not superimposed, and out of focus. Each additional sweep, i.e., a trace and a retrace (FIG. 3) would display the same point once again, and the more times that same point is superimposed and displayed at the same location, the more intense the image of that point would be as opposed to the situation where the image of a point is displayed over a larger area, thus resulting in faint and blurred images.

Referring again to FIG. 5, points $A^1$ and $A^2$ are superimposed and in focus, whereas points $B^1$ and $B^2$ are out of focus.

Figure 6:
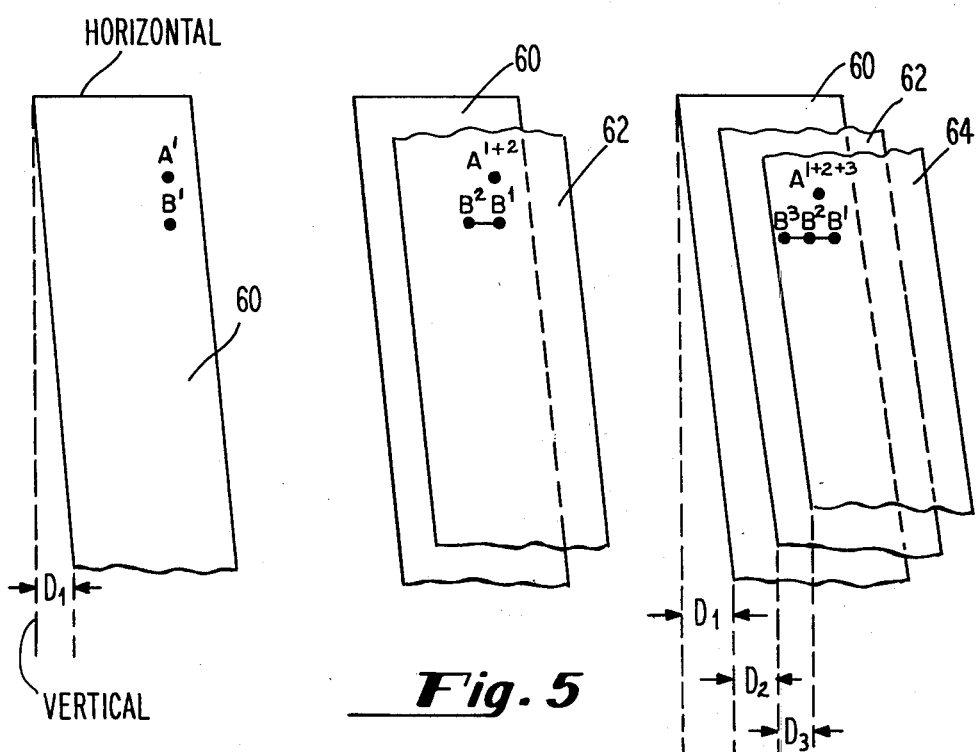

In FIG. 6, imaginary points $A^1$, $A^2$ and $A^3$ are superimposed on imaginary image frame 64, while points $B^1$, $B^2$ and $B^3$ are out of focus. Distances $D_1$, $D_2$ and $D_3$ are each approximately 0.0005", or substantially equivalent to the distance the input screen of detector 16 travels while orbiting on arm 24 while detector 16 scans an image frame 64, for example, from top to bottom. The distance $D_1$ is calculated by multiplying 10" by the quotient obtained when dividing 1 millisecond by 20 seconds.

A high persistence oscilloscope screen may or may not be employed in conjunction with display screens 20 and 21 and the system may further include a memory tube with or without hard film permanent record, motion picture film record, tape storage, holographic storage, or any other conventionally available high resolution permanent storage media. If short persistence screens are used, an oscilloscope camera C is needed for each display in order to display a full 5"×10" view. No real time display will be provided in this instance as the image is recorded and viewed on the film.

As aforementioned, a complete panoramic scan requires about 20 seconds. Hence, if a conventional non-memory oscilloscope is used, it becomes necessary to either utilize a very long persistence phosphor to provide a real time display, or photograph the image as the slot image moves across the screen. Alternatively, a memory scope could be utilized such that the display would be created in front of the viewer, and then retained. Typical memory scopes can readily retain a display pattern for an hour or longer, thus allowing ample time for careful study, photographs, and the like. Of course, once the screen is blanked, all intelligence thereon is lost unless recorded on film or other suitable media.

Further the invention lends itself readily to the use of electronic memory storage wherein the radiographic data may be stored to thus permit the stored information to be recalled and displayed repeatedly at will, wherein magnification and contrast of images are easily varied to optimize areas of interest to thus provide differing images and real time displays with only a single panoramic scan. If a single display or multiple displays without memory are used, or if an electronic memory is used, the clinician may adjust appropriate controls to change waveshapes of the low frequency horizontal deflection voltages to thus change the display view and focal trough in real time as the image forms on the display screen, i.e., the area of sharpest focus may be moved in and out until the area of interest is displayed in optimum fashion. Hence, many different images may be made from a single exposure of the patient resulting in enhancement of diagnostic information. Further, an operator, with practice, is expected to be able to recognize anatomical landmarks and to adjust the focal trough in real time as the display forms on the screen in approximately 20 seconds, or longer, or shorter, as desired.

Additionally, various image intensification means may be incorporated into the present detector 16 system to even further reduce radiation dosages to the patient.

While several embodiments of my invention are illustrated and described, it will be apparent that changes and modifications may be made therein without departing from the spirit and scope thereof.

For example, the present system could be made to include a constant magnification approach, i.e., each different focal trough selected would automatically change the physical length of display upon the oscilloscope screen to provide a predetermined magnification. In such case, the low frequency sweep voltage frequency as well as its wave shape would both change with changing focal troughs.

Or, the present system could be made to employ an automatic feedback type focus control system, i.e., once the built-in capability of dynamically varying the focal trough is present, as in the instant system, an appropriate indicator of proper focus may be selected and then the focal trough may automatically be varied as an image is created on the screen to assure that the areas of interest are in proper focus to thus minimize any need for manual adjustments.

Of course, further modifications will be apparent to those skilled in the art, and it is intended that the invention be limited only as indicated by the scope of the claims.

I claim:

1. A method of providing simultaneous multiple panoramic tomographic images of focal trough of a patient's dental arch by means of exposure thereto of X-radiation from a single continuous X-ray panoramic scan of said dental arch wherein said patient is seated in a chair capable of movement in the path of said X-radiations which are generated from a stationary X-ray origin point traveling in a circular orbit about said patient's dental arch, said X-radiations passing through a collimating slot immediately subsequent to passing through said dental arch, the combination therewith of the improvement comprising the steps of detecting said X-radiations passing through said slot by detector sweeps to form electric signals proportional to intensity of the detected X-radiations, said electric signals being representative of a slot image of said dental arch being instantaneously panoramically scanned by said X-radiations, directing said signals representing said instantaneous slot image into an oscilloscope display screen while simultaneously sweeping successive instantaneous slot images representative of said dental arch being panoramically scanned across length of said display screen in a period of time substantially equivalent to period of time of said circular orbit by means of a wobbulated sweep generator, synchronizing said detector sweeps and display sweeps to insure proper relative positioning of said slot images on said display screen, and adjusting said wobbulated sweeps on said display screen to sharply focus a tomographic area of interest of said dental arch.

2. The method of claim 1 wherein a different panoramic radiographic image is provided simultaneously on each of two or more display screens connected in parallel, each of said screens having a separate wobbulated sweep generator associated therewith for providing differing sweep voltages thereto for sharply focusing panoramic images of different layers or planes of said focal trough.

3. The method of claim 2 wherein said slot and said slot image are each approximately $\frac{1}{4}'' \times 5''$.

4. The method of claim 3 wherein said display screen is approximately $5'' \times 10''$.

5. The method of claim 4 wherein said wobbulated sweep comprises a low frequency horizontal sweep and a high frequency horizontal sweep and a vertical sweep, said horizontal sweeps being superimposed.

6. The method of claim 5 wherein said superimposed horizontal sweep requires no more than about 20 seconds to sweep said successive slot images across length of said display screen.

7. The method of claim 6 wherein sweeping of said successive images across length of said display screen is non-linear.

8. The method of claim 2 further characterized by the step of amplifying said electronic signals which have been formed from the detected X-radiations.

9. The method of claim 8 further characterized by the steps of directing said amplified signals into a memory store prior to display of said signals, said memory store storing patient data for the entire single panoramic X-ray scan of said patient, and creating a multiplicity of panoramically focused images simultaneously on said display screens of said focal trough from said memory store by the further step of applying wobbulated sweep voltages to said stored signals.

10. The method of claim 9 wherein said step of creating a multiplicity of panoramically focused images simultaneously on said display screens is further characterized by said focused images being amenable to a plurality of differing signal conditioning techniques.

11. The method of claim 2 wherein said focused images are amenable to a plurality of differing signal conditioning techniques.

12. The method of claim 2 further characterized by the step of creating real time changes in location of said focal trough as images thereof are being instantaneously created.

13. Apparatus for providing simultaneous multiple panoramic images of focal trough of a patient's dental arch by means of exposure thereto of X-radiation from a single continuous X-ray panoramic scan of said dental arch wherein said patient is seated in a chair capable of movement in the path of said X-radiations which are generated from a stationary X-ray origin point traveling in a circular orbit about said patient's dental arch, said X-rādiations passing through a collimating slot immediately subsequent to passing through said dental arch, the combination therewith of the improvement comprising detecting means for forming electric signals proportional to intensity of X-radiations passing through said slot, amplifying means for controlling intensity of said formed electric signals from said detecting means, display means for panoramically displaying said amplified signals in the form of instantaneous successive images having dimensions approximating said slot, said instantaneous successive images being representative of respective position of said X-ray origin point and said detecting means while panoramically scanning said dental arch, a wobbulated sweep generator for applying horizontal and vertical sweep voltages into said display means for tomographically focusing a desired plane of said focal trough image, said display means and detector means having synchronized sweeps to insure proper relative positioning of images on input screen of said detector means and said display means.

14. The apparatus of claim 13 further characterized by another wobbulated sweep generator for applying horizontal and vertical sweep voltages into another display screen connected in parallel to said other display screen.

15. The apparatus of claim 14 wherein a memory store is interposed between said amplifying means and display means for electronically storing data from said single panoramic scan of said dental arch.

16. The apparatus of claim 15 wherein said memory store cooperates with high resolution permanent storage media.

* * * * *